(12) United States Patent
Huh

(10) Patent No.: US 9,155,919 B2
(45) Date of Patent: Oct. 13, 2015

(54) INFORMATION DISPLAY AND CONTROL DEVICE OF POWERED AIR PURIFYING RESPIRATOR

(71) Applicant: OTOS WING CO., LTD., Seoul (KR)

(72) Inventor: Moon Young Huh, Seoul (KR)

(73) Assignee: OTOS WING CO., LTD. (KR)

( * ) Notice: Subject to any disclaimer, the term of this patent is extended or adjusted under 35 U.S.C. 154(b) by 445 days.

(21) Appl. No.: 13/672,767

(22) Filed: Nov. 9, 2012

(65) Prior Publication Data

US 2013/0118487 A1  May 16, 2013

(30) Foreign Application Priority Data

Nov. 11, 2011 (KR) .......................... 10-2011-117838

(51) Int. Cl.
- *A61M 16/00* (2006.01)
- *A62B 9/00* (2006.01)
- *A62B 7/10* (2006.01)
- *A62B 18/00* (2006.01)
- *A62B 18/04* (2006.01)
- *A61F 9/06* (2006.01)
- *A62B 23/02* (2006.01)

(52) U.S. Cl.
CPC . *A62B 9/006* (2013.01); *A61F 9/06* (2013.01); *A62B 7/10* (2013.01); *A62B 18/006* (2013.01); *A62B 18/04* (2013.01); *A62B 18/045* (2013.01); *A62B 23/02* (2013.01)

(58) Field of Classification Search
None
See application file for complete search history.

(56) References Cited

U.S. PATENT DOCUMENTS

| | | | | |
|---|---|---|---|---|
| 5,996,422 A | * | 12/1999 | Buck et al. | 73/863.03 |
| 6,849,049 B2 | * | 2/2005 | Starr et al. | 600/538 |
| 2005/0004711 A1 | * | 1/2005 | Hirose | 700/265 |
| 2009/0227887 A1 | * | 9/2009 | Howard et al. | 600/531 |
| 2009/0266361 A1 | * | 10/2009 | Bilger et al. | 128/204.21 |

FOREIGN PATENT DOCUMENTS

KR  1020050074391  7/2005

* cited by examiner

*Primary Examiner* — Tan-Uyen (Jackie) T Ho
*Assistant Examiner* — Eric Bryant
(74) *Attorney, Agent, or Firm* — Cantor Colburn LLP

(57) ABSTRACT

An information display and control device of an air purifying respirator comprises: a blower motor; a pulse width modulation drive unit controlling rotation of the blower motor; a temperature sensor; an air flow sensor; an oxygen sensor; a voltage detection unit for a battery; a differential pressure sensor detecting a differential pressure value of a filter; a switch input unit for a user to input predetermined temperature, air flow, and oxygen amount and operation commands; a controller executing a diagnostic mode, calibrating the oxygen sensor, calculating a detected value of the voltage detection unit to determine whether the voltage is low, comparing the detected value of the differential pressure sensor with a reference to determine whether the filter is absent or clogged, and comparing the detected value of the oxygen sensor with a reference to determine whether oxygen is insufficient or excessive; and an alarm output unit outputting an alarm.

7 Claims, 7 Drawing Sheets

1) START AND END SCREEN

INFORMATION DISPLAY AND CONTROL DEVICE OF POWERED AIR PURIFYING RESPIRATOR

BACKGROUND OF THE INVENTION

1. Field of the Invention

The present invention relates to an information display and control device of a powered air purifying respirator including a filter device for filtering off a toxic substance contained in air and a blower device for suctioning and supplying the filtered air to the air purifying respirator.

2. Description of the Related Art

A powered air purifying respirator system includes a filter device for filtering off a toxic substance contained in air and a blower device for suctioning and supplying the filtered air to an air purifying respirator. The blower device is configured to uniformly supply air to the air purifying respirator. The blower device detects clogging of a filter due to external foreign matter to correct air flow. A user may periodically inspect air flow using an air flow display device provided together with the blower device when the user buys the blower device.

Generally, a worker puts the blower device on the back of the worker using a belt. The worker puts the air purifying respirator and the blower device on, and connects the air purifying respirator to the blower using a hose. The powered air purifying respirator system is configured to detect discharge of a battery during operation, clogging of the filter due to abnormality of the filter, or the change of air flow due to foreign matter and to transmit the detected result to sensory organs of the user in the form of a sound or others so that the worker can rapidly take proper measures.

In conventional inspection of air flow, whether the blower device is operated at an air flow level required by a manufacturer is simply displayed using a separately manufactured air flow display device. In conventional correction of air flow, the change in current and the number of rotations of a motor due to pressure at the filter and the air purifying respirator is detected to correct air flow. Alternatively, an air flow sensor may be mounted to correct air flow.

In such a conventional art, however, an error may be generated due to change of air temperature and atmospheric pressure, and different amounts of air may be generated at a correction step of correcting clogging of the filter due to the pressure difference between the air flow display device and the air purifying respirator.

Also, the manufacturer detects the change of air flow in a state in which an outlet of the blower device is fully closed using a hand to inspect whether an alarm is given with respect to low air flow. However, it is not possible to display a clogging rate of the filter.

For reference, a portable air supply apparatus is disclosed in Korean Patent Application Publication No. 10-2005-0074391 (published on Jul. 18, 2005).

SUMMARY OF THE INVENTION

Therefore, the present invention has been made in view of the above problems, and it is an object of the present invention to provide an information display and control device of a powered air purifying respirator wherein air flow of a blower device is electronically detected using a precision air flow sensor mounted to the blower device without using an air flow display device, and a graphic screen that is capable of displaying an air flow level meter is displayed on the blower device or an additionally manufactured remote controller so that the air flow of the blower device can be checked during operation, thereby easily and correctly recognizing system information and taking proper measures.

It is another object of the present invention to provide an information display and control device of a powered air purifying respirator including a bi-directional wireless or specially manufactured cable type remote controller that is capable of allowing a worker to inspect an air flow state, to detect remaining battery power and expected use time, and to manipulate a blower device and exchanging information even in a state in which the worker wears the air purifying respirator and the blower device, wherein it is possible to control a designated electronic welding surface through infrared or wireless communication, and the remote controller is mounted to a belt or a designated position to prevent separation and loss of the remote controller and in consideration of operations based on switch errors.

In accordance with the present invention, the above and other objects can be accomplished by the provision of an information display and control device of a powered air purifying respirator including a blower motor for supplying air passing through a filter to a worker, a pulse width modulation (PWM) drive unit for controlling rotational velocity of the blower motor based on a predetermined value of air flow, a temperature sensor for detecting temperature, an air flow sensor for detecting air flow, an oxygen sensor for detecting an amount of oxygen, a voltage detection unit for detecting voltage of a battery, a differential pressure sensor for detecting a differential pressure value of the filter, a hose detection unit for detecting a connection state of a connection hose, a switch input unit for allowing a user to input predetermined values of temperature, air flow, and an amount of oxygen and operation commands, such as power on and power off, a controller for executing a diagnostic mode in which a total accumulated use time, a filter use time, a final error code, and the number of times of accumulated occurrence of errors are calculated and displayed, calibrating the oxygen sensor, calculating the detected value of the voltage detection unit to determine whether the voltage of the battery is low, comparing the detected value of the differential pressure sensor with a reference value to determine whether the filter is absent or clogged, and comparing the detected value of the oxygen sensor with a reference value to determine whether oxygen is insufficient or excessive, a screen display unit for displaying the air flow detected by the air flow sensor, the amount of oxygen detected by the oxygen sensor, and various errors states, such as clogging of the filter and insufficiency of oxygen, an alarm output unit for outputting an alarm when various errors states, such as clogging of the filter and insufficiency of oxygen, occur, and a vibration motor for generating vibration.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Now, a preferred embodiment of the present invention will be described in detail with reference to the accompanying drawings.

Figure 1:
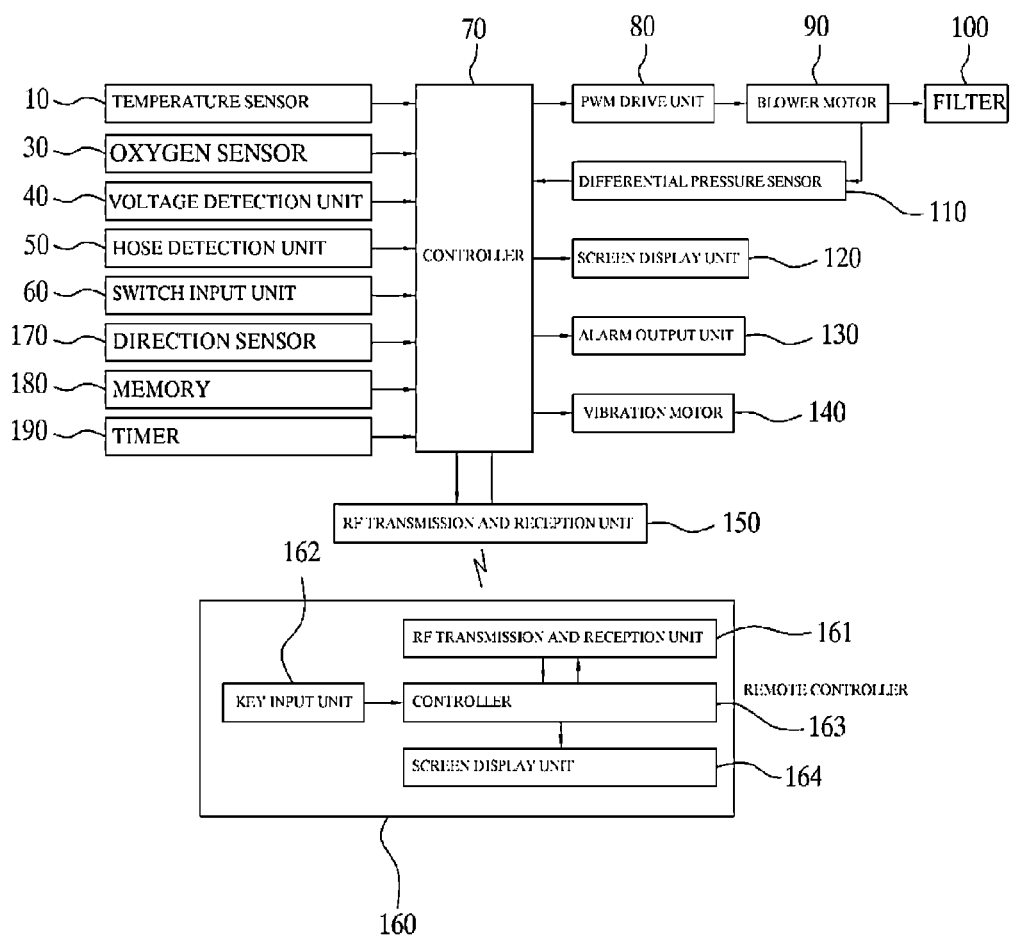
FIG. 1 is a block diagram showing an information display and control device of a powered air purifying respirator according to the present invention.
Figure 2:
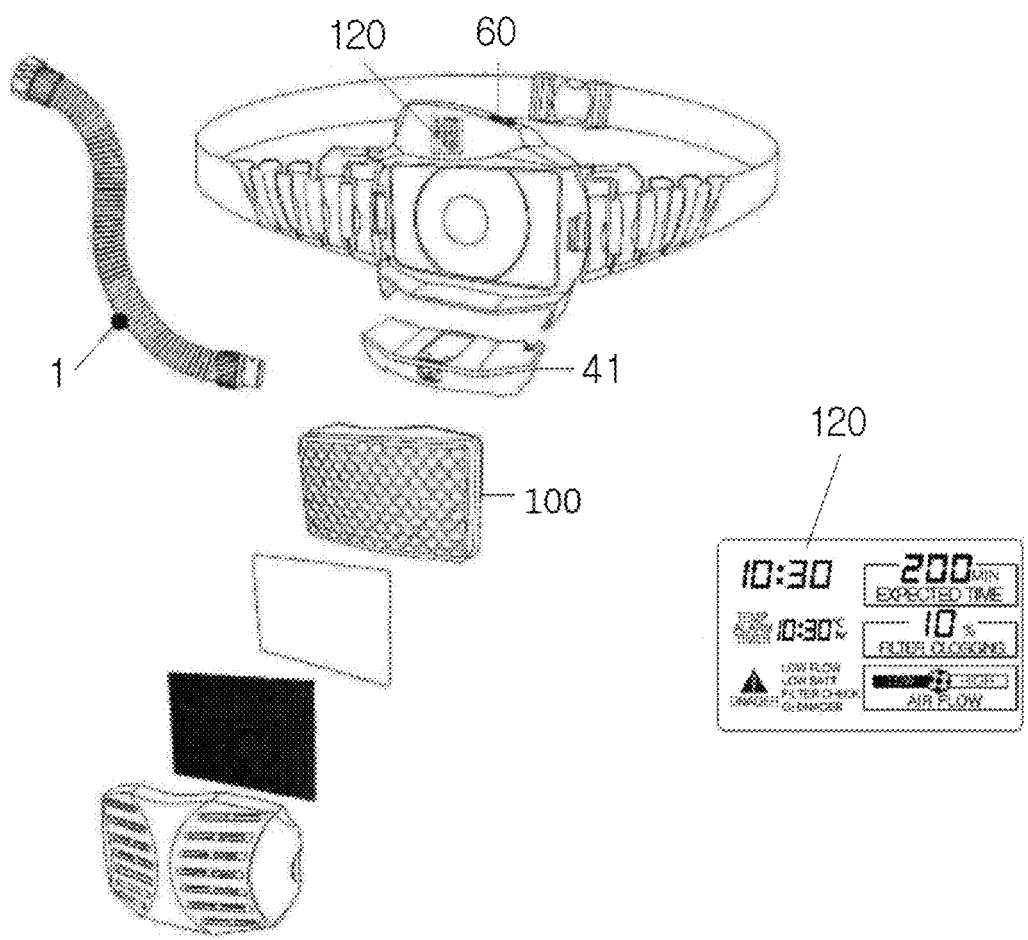
FIG. 2 is a perspective view showing an external construction of the information display and control device of the powered air purifying respirator according to the present invention.
Figure 3:
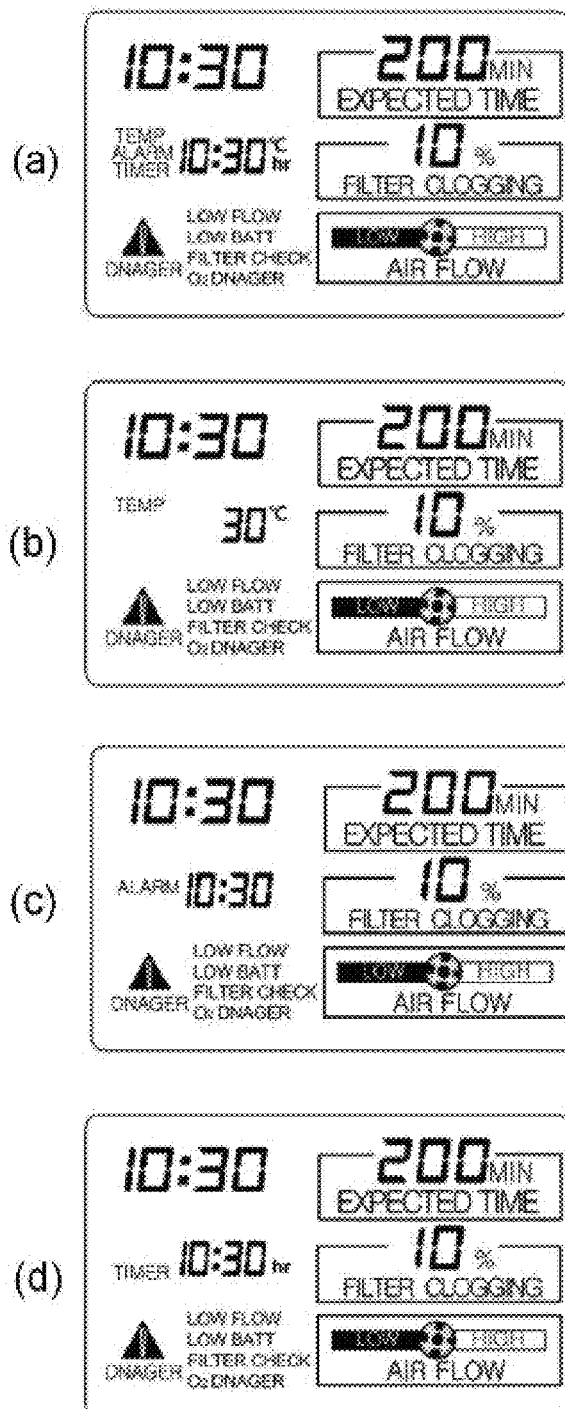
FIG. 3 is a view showing display screen constructions of the information display and control device of the powered air purifying respirator according to the present invention.
Figure 4:
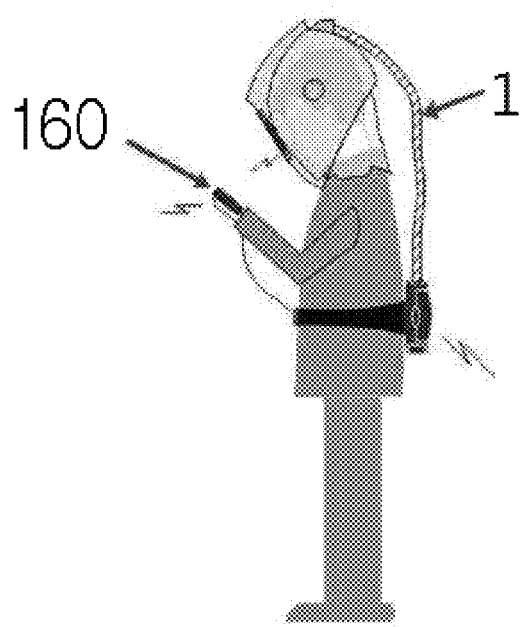
FIG. 4 is a view showing a state in which a user wears the information display and control device of the powered air purifying respirator according to the present invention.
Figure 5:
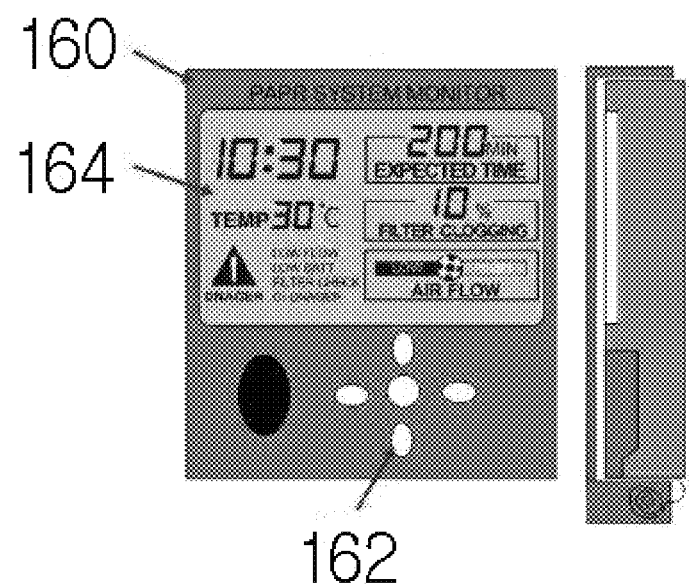
FIG. 5 is a front view and side view showing a remote controller of the information display and control device of the powered air purifying respirator according to the present invention.

FIG. 1 is a block diagram showing an information display and control device of a powered air purifying respirator according to the present invention, FIG. 2 is a perspective view showing an external construction of the information display and control device of the powered air purifying respirator according to the present invention, FIG. 3 is a view showing display screen constructions of the information display and control device of the powered air purifying respirator according to the present invention, FIG. 4 is a view showing a state in which a user wears the information display and control device of the powered air purifying respirator according to the present invention, and FIG. 5 is a front view and side view showing a remote controller of the information display and control device of the powered air purifying respirator according to the present invention.

As shown, the information display and control device of the powered air purifying respirator according to the present invention includes a blower motor 90 for supplying air passing through a filter 100 to a worker, a pulse width modulation (PWM) drive unit 80 for controlling rotational velocity of the blower motor 90 based on a predetermined value of air flow, a temperature sensor 10 for detecting temperature, an air flow sensor 20 for detecting air flow, an oxygen sensor 30 for detecting an amount of oxygen, a voltage detection unit 40 for detecting voltage of a battery 41, a differential pressure sensor 110 for detecting a differential pressure value of the filter 100, a hose detection unit 50 for detecting a connection state of a connection hose 1, a switch input unit 60 for allowing a user to input predetermined values of temperature, air flow, and an amount of oxygen and operation commands, such as power on and power off, a controller 70 for executing a diagnostic mode in which a total accumulated use time, a filter use time, a final error code, and the number of times of accumulated occurrence of errors are calculated and displayed, calibrating the oxygen sensor 30, calculating the detected value of the voltage detection unit 40 to determine whether the voltage of the battery 41 is low, comparing the detected value of the differential pressure sensor 110 with a reference value to determine whether the filter is absent or clogged, and comparing the detected value of the oxygen sensor 30 with a reference value to determine whether oxygen is insufficient or excessive, a screen display unit 120 for displaying the air flow detected by the air flow sensor 20, the amount of oxygen detected by the oxygen sensor 30, and various errors states, such as clogging of the filter and insufficiency of oxygen, an alarm output unit 130 for outputting an alarm when various errors states, such as clogging of the filter and insufficiency of oxygen, occur, and a vibration motor 140 for generating vibration.

In order to calibrate the oxygen sensor 30, the controller 70 calculates a value of C according to mathematical expressions 1 and 2 below to perform linearity calibration.

$$S = K \times \ln\left(\frac{1}{1-C}\right)$$ [Mathematical expression 1]

$$C = 1 - \frac{1}{\exp\left(\frac{S}{K}\right)}$$ [Mathematical expression 2]

Where, S indicates an output signal, C indicates fractional $O_2$ concentration, and K indicates a constant for the sensor.

Also, the information display and control device of the powered air purifying respirator according to the present invention further includes a radio frequency (RF) transmission and reception unit 150 for transmitting and receiving data obtained as the result of the calculation and determination performed by the controller 70 in a wireless fashion and a remote controller 160 for transmitting and receiving data to and from the RF transmission and reception unit 150 in a wireless fashion, allowing a user to remotely input predetermined values of temperature, air flow, and an amount of oxygen and operation commands, such as power on and power off, and displaying an amount of oxygen and various errors states, such as clogging of the filter and insufficiency of oxygen.

The remote controller 160 includes an RF transmission and reception unit 161 for transmitting and receiving data to and from the RF transmission and reception unit 150 in a wireless fashion, a key input unit 162 for a user to remotely input predetermined values of temperature, air flow, and an amount of oxygen and operation commands, such as power on and power off, a screen display unit 164 for displaying an amount of oxygen and various errors states, such as clogging of the filter and insufficiency of oxygen, and a controller 163 for controlling operations of the respective units of the remote controller 160.

Also, the information display and control device of the powered air purifying respirator according to the present invention further includes a direction sensor 170 for detecting a direction, and the controller 70 controls the direction detected by the direction sensor 170 to be displayed on the screen display unit 120 so that a user can be aware of where the user is in a work area.

Also, the information display and control device of the powered air purifying respirator according to the present invention further includes a memory 180 for storing operation commands and operation states in many languages, and the controller 70 controls one selected from among the many languages stored in the memory 180 to be displayed on the screen display unit 120.

Also, the information display and control device of the powered air purifying respirator according to the present invention further includes a timer 190 for counting time, and the controller 70 controls current time based on the time counted by the timer 190 and alarm, timer, and stopwatch functions to be displayed on the screen display unit 120.

Also, the controller 70 may control an accumulated work time based on the time counted by the timer 190 to be displayed on the screen display unit 120.

Figure 6:
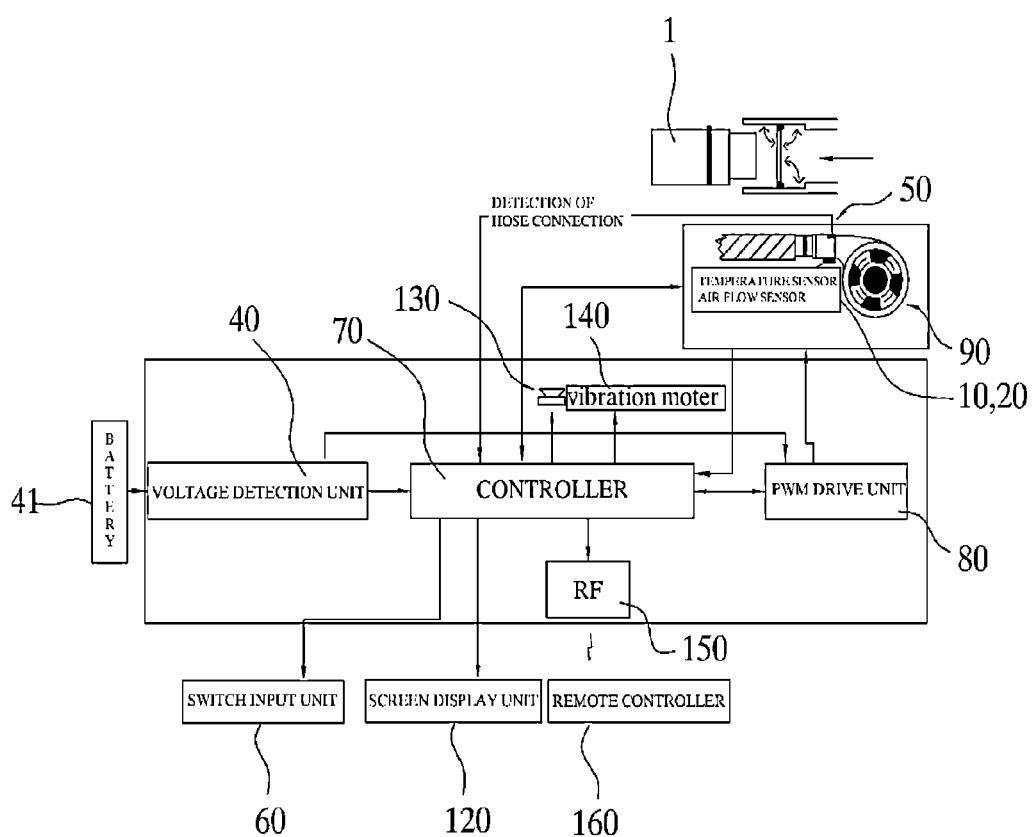
FIG. 6 is a block diagram showing an embodiment of the information display and control device of the powered air purifying respirator according to the present invention.
Figure 7:
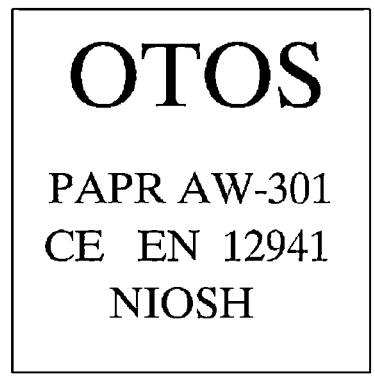
FIG. 7 is a view showing an embodiment of a start and end screen construction of the information display and control device of the powered air purifying respirator according to the present invention.

1. Function setting and operation of the information display and control device of the powered air purifying respirator according to the present invention are as follows.
   1) Kinds of function keys
   K1 (ON or OFF)
   K2 (Weak or Decrease)
   K3 (Strong or Increase)
   2) Power ON
   3) Power OFF
   4) Change of air flow
   5) Oxygen sensor calibration mode
   6) Completion of oxygen sensor calibration
   7) Initialization of accumulated filter use time
   8) Air flow setting mode
   9) Air flow setting: selection of weak or strong
   10) Increase or decrease of air flow set value
   11) Completion of air flow setting
   12) Confirmation of diagnostic mode
   13) Initialization of diagnostic mode
   14) Completion of confirmation of diagnostic mode
   15) Selection of LCD display direction FIG. 6 is a block diagram showing an embodiment of the information display and control device of the powered air purifying respirator according to the present invention, and FIG. 7 is a view showing an embodiment of a start and end screen construction of the information display and control device of the powered air purifying respirator according to the present invention.

Upon performing a final key input, a screen is displayed for a predetermined period of time and is then automatically turned OFF.

If a key input is performed or a dangerous condition occurs in a state in which the display is OFF during operation, the display is turned ON.

If a dangerous state occurs during operation, a basic screen and a danger display screen are alternately displayed.

Type of filter: The type of a filter which has been automatically detected is displayed (Dust type, gas type, or combination type)

Accumulated filter use time: An accumulated filter use time is displayed. If a new filter is detected, the accumulated filter use time is automatically initialized.

2. Method of Calibrating and Detecting Oxygen Sensor

Linearity calibration of the oxygen sensor (example, a capillary hole type oxygen sensor) is performed as follows. In order to perform linearity calibration of the capillary hole type oxygen sensor, it is necessary to finally calculate a value of C from mathematical expressions 1 and 2 below.

$$S = K \times \ln\left(\frac{1}{1-C}\right) \quad \text{[Mathematical expression 1]}$$

Where, S indicates an output signal, C indicates fractional $O_2$ concentration, and K indicates a constant for the sensor.

The value of C may be calculated from the following mathematical expression. After linearity calibration of the oxygen sensor is performed using these mathematical expressions, therefore, the instrument is tested.

$$C = 1 - \frac{1}{\exp\left(\frac{S}{K}\right)} \quad \text{[Mathematical expression 2]}$$

3. Detection of Remaining Battery Power
   1) Display of Remaining Battery Power The remaining battery power is displayed as a stepwise graph based on input voltage of a battery voltage detection circuit.

Detected voltage of the battery is changed depending upon used current and temperature and thus is based on the following graph.

If low voltage of the battery is detected during operation, the operation is continued in a state in which an error screen is alternately displayed.

4. Control of Air Flow Based on Differential Pressure Sensor
   1) Method of Detecting Type of the Filter Upon power ON, a PWM value is output.

Subsequently, the type of the filter and a connection state of the filter are detected based on a signal input from the differential pressure sensor.

If the type of the filter is detected, the detected type of the filter is displayed, and proportional-integral-derivative (PID) control based on predetermined air flow is commenced.

If a value other than basic filters is input, an error screen is displayed, and the operation is turned OFF.

2) Method of Detecting Clogging or Abnormality of the Filter

Upon completing filter type detection, a PWM output suitable for reference differential pressure is controlled based on PID control to control the selected air flow.

The detection method is performed within a range of the PWM output to maintain reference air flow.

If abnormality of the filter is detected during operation, the operation is continued in a state in which an error screen is alternately displayed.

As is apparent from the above description, according to the information display and control device of the powered air purifying respirator with the above-stated construction according to the present invention, air flow of a blower device is electronically detected using a precision air flow sensor mounted to the blower device without using an air flow display device, and a graphic screen that is capable of displaying an air flow level meter is displayed on the blower device or an additionally manufactured remote controller so that the air flow of the blower device can be checked during operation, thereby easily and correctly recognizing system information and taking proper measures.

Also, the information display and control device of the powered air purifying respirator according to the present invention includes a bi-directional wireless or specially manufactured cable type remote controller that is capable of allowing a worker to inspect an air flow state, to detect remaining battery power and expected use time, and to manipulate a blower device and exchanging information even in a state in which the worker wears the air purifying respirator and the blower device, wherein it is possible to control a designated electronic welding surface through infrared or wireless communication, and the remote controller is mounted to a belt or a designated position to prevent separation and loss of the remote controller and in consideration of operations based on switch errors.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

What is claimed is:

1. An information display and control device of a powered air purifying respirator comprising:
   a blower motor for supplying air passing through a filter to a worker;
   a pulse width modulation (PWM) drive unit for controlling rotational velocity of the blower motor based on a predetermined value of air flow;
   a temperature sensor for detecting temperature;
   an air flow sensor for detecting air flow;
   an oxygen sensor for detecting an amount of oxygen;
   a voltage detection unit for detecting voltage of a battery;
   a differential pressure sensor for detecting a differential pressure value of the filter;
   a hose detection unit for detecting a connection state of a connection hose;
   a switch input unit for allowing a user to input predetermined values of temperature, air flow, and an amount of oxygen and operation commands, including power on and power off;
   a controller for executing a diagnostic mode in which a total accumulated use time, a filter use time, a final error code, and a number of times of accumulated occurrence of errors are calculated and displayed, calibrating the oxygen sensor, calculating a detected value of the voltage detection unit to determine whether the voltage of the battery is low, comparing the detected value of the differential pressure sensor with a reference value to determine whether the filter is absent or clogged, and comparing the detected value of the oxygen sensor with a reference value to determine whether oxygen is insufficient or excessive;
   a screen display unit for displaying the air flow detected by the air flow sensor, the amount of oxygen detected by the oxygen sensor, and various errors states, including clogging of the filter and insufficiency of oxygen;
   an alarm output unit for outputting an alarm when various errors states, including clogging of the filter and insufficiency of oxygen, occur; and
   a vibration motor for generating vibration.

2. The information display and control device of the powered air purifying respirator according to claim 1, wherein the controller calculates a value of C according to mathematical expressions 1 and 2 below to perform linearity calibration, thereby calibrating the oxygen sensor.

$$S = K \times \ln\left(\frac{1}{1-C}\right) \quad \text{[Mathematical expression 1]}$$

$$C = 1 - \frac{1}{\exp\left(\frac{S}{K}\right)} \quad \text{[Mathematical expression 2]}$$

where, S indicates an output signal, C indicates fractional $O_2$ concentration, and K indicates a constant for the oxygen sensor.

3. The information display and control device of the powered air purifying respirator according to claim 1, further comprising:
   a radio frequency (RF) transmission and reception unit for transmitting and receiving data obtained as a result of calculation and determination performed by the controller in a wireless fashion; and
   a remote controller for transmitting and receiving data to and from the RF transmission and reception unit in a wireless fashion, allowing a user to remotely input predetermined values of temperature, air flow, and an amount of oxygen and operation commands, such as including power on and power off, and displaying an amount of oxygen and various errors states, such as including clogging of the filter and insufficiency of oxygen.

4. The information display and control device of the powered air purifying respirator according to claim 1, further comprising a direction sensor for detecting a direction, wherein the controller controls the direction detected by the direction sensor to be displayed on the screen display unit so that a user can be is aware of where the user is in a work area.

5. The information display and control device of the powered air purifying respirator according to claim 1, further comprising a memory for storing operation commands and operation states in many languages, wherein the controller controls one selected from among the many languages stored in the memory to be displayed on the screen display unit.

6. The information display and control device of the powered air purifying respirator according to claim 1, further comprising a timer for counting time, wherein the controller controls current time based on the time counted by a timer and alarm, timer, and stopwatch functions to be displayed on the screen display unit.

7. The information display and control device of the powered air purifying respirator according to claim 6, wherein the controller controls an accumulated work time based on the time counted by the timer to be displayed on the screen display unit.

* * * * *